(12) United States Patent
Claremon et al.

(10) Patent No.: US 6,440,976 B2
(45) Date of Patent: Aug. 27, 2002

(54) IMINOPYRIMIDINE NMDA NR2B RECEPTOR ANTAGONISTS

(75) Inventors: David A. Claremon; John A. McCauley, both of Maple Glen; Nigel J. Liverton, Harleysville, all of PA (US); Cory R. Theberge, Dover, NH (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/888,694

(22) Filed: Jun. 25, 2001

Related U.S. Application Data
(60) Provisional application No. 60/214,654, filed on Jun. 26, 2000.

(51) Int. Cl.[7] ............... C07D 239/42; C07D 403/04; A61K 31/505; A61K 31/506

(52) U.S. Cl. .............. 514/256; 514/248; 514/249; 514/252.02; 544/326; 544/327; 544/328; 544/295; 544/296

(58) Field of Search ............... 544/326, 327, 544/328, 295, 296; 514/248, 249, 252.02, 256

(56) References Cited
PUBLICATIONS

Kristensen et al., Pain, 51: 249–253 (1992).
K. Eide et al., Pain, 61: 221–228(1995).
D.J. Knox et al., Andesth, Intensive Care, 23: 620–622(1995).
M.B. Max et al. Clin. Neuropharmacol., 18: 360–368(1995).
I. Ishii et al., J. Biol. Chem., 268: 2836–2843.
A. Wenzel et al., Neural Report, 7: 45–48(1995).
D.J. Laurie et al., Mol. Brain Research, 51: 23–329(1997).
S. Boyce et al., Neuropharmacology, 33: 611–623(1999).
J. A. McCauley, et al. Org. Lett., 2: 3389–3391(2000).

*Primary Examiner*—John M. Ford
(74) *Attorney, Agent, or Firm*—Shu Muk Lee; David L. Rose

(57) ABSTRACT

Compounds described by the chemical structural formula

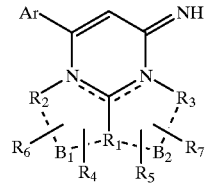

or a pharmaceutically acceptable salt thereof, are useful in the treatment of pain, migraine, depression, anxiety, schizophrenia, Parkinson's disease, stroke, and in the treatment of neuropathies including postherpetic neuralgia, central pain from spinal cord injury, and phantom limb pain.

8 Claims, No Drawings

IMINOPYRIMIDINE NMDA NR2B RECEPTOR ANTAGONISTS

This application claims priority from provisional application Ser. No. 60/214,654, filed Jun. 26, 2000.

BACKGROUND OF THE INVENTION

1. Field of the Invention

This invention relates to novel iminopyrimidine compounds. In particular, this invention relates to novel iminopyrimidine compounds effective as NMDA NR2B antagonists.

2. Related Background

Ions play a key role in processes related to chronic pain and pain-associated neurotoxicity—primarily by acting through N-methyl-D-aspartate ("NMDA") receptors. Thus, inhibition of such action—by employing ion channel antagonists, particularly NMDA antagonists—can be beneficial in the treatment and control of pain.

Known NMDA antagonists include ketamine, dextromophan, and 3-(2-carboxypiperazin-4-yl)-propyl-1-phosphonic acid ("CPP"). Although these compounds have been reported (J. D. Kristensen, et al., *Pain*, 51:249–253 (1992); K. Eide, et al., *Pain*, 61:221–228 (1995); D. J. Knox, et al., *Anaesth. Intensive Care* 23:620-622 (1995); and M. B. Max, et al., *Clin. Neuropharmacol.* 18:360–368 (1995)) to produce symptomatic relief in a number of neuropathies including postherpetic neuralgia, central pain from spinal cord injury, and phantom limb pain, widespread use of these compounds is precluded by their undesirable side effects. Such side effects at analgesic doses include psychotomimetic effects such as dizziness, headache, hallucinations, dysphoria, and disturbances of cognitive and motor function. Additionally, more severe hallucinations, sedation, and ataxia are produced at doses only marginally higher than analgesic doses. Thus, it would be desirable to provide novel NMDA antagonists that are absent of undesirable side effects or that produce fewer and/or milder side effects.

NMDA receptors are heteromeric assemblies of subunits, of which two major subunit families designated NR1 and NR2 have been cloned. Without being bound by theory, it is generally believed that the various functional NMDA receptors in the mammalian central nervous system ("CNS") are only formed by combinations of NR1 and NR2 subunits, which respectively express glycine and glutamate recognition sites. The NR2 subunit family is in turn divided into four individual subunit types: NR2A, NR2B, NR2C, and NR2D. L. Ishii, et al., *J. Biol. Chem.*, 268:2836–2843 (1993), A. Wenel, et al., *Neural Report*, 7:45–48 (1995), and D. J. Laurie et al., *Mol. Brain Res.*, 51:23–32 (1997) describe how the various resulting combinations produce a variety of NMDA receptors differing in physiological and pharmacological properties such as ion gating properties, magnesium sensitivity, pharmacological profile, as well as in anatomical distribution.

For example, while NR1 is found throughout the brain, NR2 subunits are differentially distributed. In particular, it is believed that the distribution map for NR2B lowers the probability of side effects while producing pain relief. S. Boyce, et al., *Neuropharmacology*, 33:1609–1611 (1994) describes the regional distribution of the NMDA receptor contining the NR2B subunit protein in rat lumbar spinal cord. Thus, it would be desirable to provide novel NMDA antagonists that target the NR2B receptor.

SUMMARY OF THE INVENTION

Compounds described by the following chemical structural formula (I):

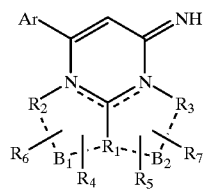

or a pharmaceutically acceptable salt thereof, wherein i) Ar is an aromatic group, the aromatic group being phenyl, naphthyl, pyridinyl, pyridazinyl, pyrimidinyl, pyrazinyl, imidazolyl, quinoxalinyl, furyl, thienyl, pyrrolyl, benzimidazolyl, indolyl, quinolinyl, isoquinolinyl, pyrazolyl, indazolyl, oxazolyl, isoxazolyl, thiazolyl, isothiazolyl, oxadiazolyl, thiadiazolyl, triazolyl, tetrazolyl, imidazolyl, benzthienyl, or benzofuryl, the aromatic group optionally substituted by one or two substituents, each substituent independently is halogen, $C_{1-4}$alkyl, or oxy$C_{1-4}$alkyl;

ii) $R_1$ is a phenyl; or —$CH_2$—, —NH—, —$NR_4$—, —$NR_5$—, or =N— when optionally connected either via $B_1$ to $R_2$ or via $B_2$ to $R_3$;

iii) $R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl; $R_2$ optionally is —$CH_2$— or =CH— connected via $B_1$ to $R_1$;

iv) $R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl; $R_3$ optionally is —$CH_2$— or =CH— connected via $B_2$ to $R_1$;

v) $R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

vi) $R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

vii) $R_6$ is a phenyl group, a $C_{1-4}$alkylphenyl group, or absent;

viii) $R_7$ is a phenyl group, a $C_{1-4}$alkylphenyl group, or absent;

ix) $B_1$ is —$CH_2$—, =CH—, —$CH_2CH_2$—, —CH=CH—, or absent; and x) $B_2$ is —$CH_2$—, =CH—, —$CH_2CH_2$—, —CH=CH—, or absent;

are useful in the treatment of pain, migraine, depression, anxiety, schizophrenia, Parkinson's disease, stroke, and in the treatment of neuropathies including postherpetic neuralgia, central pain from spinal cord injury, and phantom limb pain.

DETAILED DESCRIPTION OF THE INVENTION

The compounds of the present invention are described by the following chemical structural formula (I):

(I)

or a pharmaceutically acceptable salt thereof, wherein
  i) Ar is an aromatic group, the aromatic group being phenyl, naphthyl, pyridinyl, pyridazinyl, pyrimidinyl, pyrazinyl, imidazolyl, quinoxalinyl, furyl, thienyl, pyrrolyl, benzimidazolyl, indolyl, quinolinyl, isoquinolinyl, pyrazolyl, indazolyl, oxazolyl, isoxazolyl, thiazolyl, isothiazolyl, oxadiazolyl, thiadiazolyl, triazolyl, tetrazolyl, imidazolyl, benzthienyl, or benzofuryl, the aromatic group optionally substituted by one or two substituents, each substituent independently is halogen, $C_{1-4}$alkyl, or oxy$C_{1-4}$alkyl;
  ii) $R_1$ is a phenyl; or —$CH_2$—, —NH—, —$NR_4$—, —$NR_5$—, or =N— when optionally connected either via $B_1$ to $R_2$ or via $B_2$ to $R_3$;
  iii) $R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl; $R_2$ optionally is —$CH_2$— or =CH— connected via $B_1$ to $R_1$;
  iv) $R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl; $R_3$ optionally is —$CH_2$— or =CH— connected via $B_2$ to $R_1$;
  v) $R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;
  vi) $R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;
  vii) $R_6$ is a phenyl group, a $C_{1-4}$alkylphenyl group, or absent;
  viii) $R_7$ is a phenyl group, a $C_{1-4}$alkylphenyl group, or absent;
  ix) $B_1$ is —$CH_2$—, =CH—, —$CH_2CH_2$—, —CH=CH—, or absent; and
  x) $B_2$ is —$CH_2$—, =CH—, —$CH_2CH_2$—, —CH=CH—, or absent.

In an aspect, the compounds of this invention are described by formula (I), or a pharmaceutically acceptable salt thereof, wherein
  Ar is a phenyl ring, optionally substituted by one or two substituents, each substituent independently is halogen, $C_{1-4}$alkyl, or oxy$C_{1-4}$alkyl;
  $R_1$ is a phenyl; or $R_1$ is —$CH_2$—, —NH—, —$NR_4$—, —$NR_5$—, or =N— when optionally connected either via $B_1$ to $R_2$ or via $B_2$ to $R_3$;
  $R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl; $R_2$ optionally is —$CH_2$— or =CH— connected via $B_1$ to $R_1$;
  $R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl; $R_3$ optionally is —$CH_2$— or =CH— connected via $B_2$ to $R_1$;
  $R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;
  $R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;
  $R_6$ is a phenyl group, a $C_{1-4}$alkylphenyl group, or absent;
  $R_7$ is a phenyl group, a $C_{1-4}$alkylphenyl group, or absent;
  $B_1$ is —$CH_2$—, =CH—, —$CH_2CH_2$—, —CH=CH—, or absent; and
  $B_2$ is —$CH_2$—, =CH—, —$CH_2CH_2$—, —CH=CH—, or absent.

In one aspect, the compounds of the present invention are described by formula (I), or a pharmaceutically acceptable salt thereof, wherein
  Ar is a phenyl ring, optionally substituted by one or two substituents, each substituent independently is halogen, $C_{1-4}$alkyl, or oxy$C_{1-4}$alkyl;
  $R_1$ is a phenyl;
  $R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;
  $R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;
  $R_4$ is absent;
  $R_5$ is absent;
  $R_6$ is absent;
  $R_7$ is absent;
  $B_1$ is absent; and
  $B_2$ is absent.

In one embodiment of this aspect, the compounds of the present invention are described by formula (I), or a pharmaceutically acceptable salt thereof, wherein
  Ar is a phenyl ring, optionally substituted by one or two substituents, each substituent independently is halogen, $C_{1-4}$alkyl, or oxy$C_{1-4}$alkyl;
  $R_1$ is a phenyl;
  $R_2$ is a phenyl group, a $C_{1-4}$alkylphenyl group, wherein the groups optionally may be substituted by one or two substituents, each substituent is independently halogen, $C_{1-4}$alkyl, or oxy$C_{1-4}$alkyl;
  $R_3$ is absent;
  $R_4$ is absent;
  $R_5$ is absent;
  $R_6$ is absent;
  $R_7$ is absent;
  $B_1$ is absent; and
  $B_2$ is absent.

In another embodiment of this aspect, the compounds of the present invention are described by formula (I), or a pharmaceutically acceptable salt thereof, wherein Ar is a phenyl ring, optionally substituted by one or two substituents, each substituent independently is halogen, $C_{1-4}$alkyl, or oxy$C_{1-4}$alkyl;

$R_1$ is a phenyl;

$R_2$ is absent;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is absent;

$R_5$ is absent;

$R_6$ is absent;

$R_7$ is absent;

$B_1$ is absent; and $B_2$ is absent.

In a second aspect, the compounds of the present invention are described by formula (I) or a pharmaceutically acceptable salt thereof, wherein Ar is a phenyl ring, optionally substituted by one or two substituents, each substituent independently is halogen, $C_{1-4}$alkyl, or oxy$C_{1-4}$alkyl;

$R_1$ is —$CH_2$— connected via $B_1$ to $R_2$;

$R_2$ is —$CH_2$— or —CH= connected via $B_1$ to $R_1$;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is —$CH_2$—, =CH—, —$CH_2CH_2$—, —CH=CH—; and $B_2$ is absent.

In an embodiment of the second aspect, the compounds of the present invention are described by formula (I) or a pharmaceutically acceptable salt thereof, wherein Ar is a phenyl ring, optionally substituted by one or two substituents, each substituent independently is halogen, $C_{1-4}$alkyl, or oxy$C_{1-4}$alkyl;

$R_1$ is —$CH_2$— connected via $B_1$ to $R_2$;

$R_2$ is —$CH_2$— connected via $B_1$ to $R_1$;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent; and $B_1$ is —$CH_2$—.

In another embodiment of the second aspect, the compounds of the present invention are described by formula (I) or a pharmaceutically acceptable salt thereof, wherein Ar is a phenyl ring, optionally substituted by one or two substituents, each substituent independently is halogen, $C_{1-4}$alkyl, or oxy$C_{1-4}$alkyl;

$R_1$ is —$CH_2$— connected via $B_1$ to $R_2$;

$R_2$ is —$CH_2$— connected via $B_1$ to $R_1$;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent; and $B_1$ is —$CH_2CH_2$—.

In still another embodiment of the second aspect, the compounds of the present invention are described by formula (I) or a pharmaceutically acceptable salt thereof, wherein Ar is a phenyl ring, optionally substituted by one or two substituents, each substituent independently is halogen, $C_{1-4}$alkyl, or oxy$C_{1-4}$alkyl;

$R_1$ is —$CH_2$— connected via $B_1$ to $R_2$;

$R_2$ is —$CH_2$— connected via $B_1$ to $R_1$;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent; and $B_1$ is —CH=CH—.

In another embodiment of the second aspect, the compounds of the present invention are described by formula (I) or a pharmaceutically acceptable salt thereof, wherein Ar is a phenyl ring, optionally substituted by one or two substituents, each substituent independently is halogen, $C_{1-4}$alkyl, or oxy$C_{1-4}$alkyl;

$R_1$ is —$CH_2$— connected via $B_1$ to $R_2$;

$R_2$ is —CH= connected via $B_1$ to $R_1$;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent; and $B_1$ is =CH—.

In a third aspect of the invention, the compounds of the present invention are described by formula (I) or a pharmaceutically acceptable salt thereof, wherein Ar is a phenyl ring, optionally substituted by one or two substituents, each substituent independently is halogen, $C_{1-4}$alkyl, or oxy$C_{1-4}$alkyl;

$R_1$ is —$CH_2$— connected via $B_2$ to $R_3$;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_3$ is —$CH_2$— or —CH= connected via $B_2$ to $R_1$;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is absent; and $B_2$ is —$CH_2$—, =CH—, —$CH_2CH_2$—, —CH=CH—.

In an embodiment of the third aspect of the invention, the compounds of the present invention are described by formula (I) or a pharmaceutically acceptable salt thereof, wherein Ar is a phenyl ring, optionally substituted by one or two substituents, each substituent independently is halogen, $C_{1-4}$alkyl, or oxy$C_{1-4}$alkyl;

$R_1$ is —$CH_2$— connected via $B_2$ to $R_3$;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_3$ is —$CH_2$— connected via $B_2$ to $R_1$;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is absent; and $B_2$ is —$CH_2$—.

In another embodiment of the third aspect of the invention, the compounds of the present invention are described by formula (I) or a pharmaceutically acceptable salt thereof, wherein Ar is a phenyl ring, optionally substituted by one or two substituents, each substituent independently is halogen, $C_{1-4}$alkyl, or oxy$C_{1-4}$alkyl;

$R_1$ is —$CH_2$— connected via $B_2$ to $R_3$;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_3$ is —$CH_2$— connected via $B_2$ to $R_1$;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is absent; and $B_2$ is —$CH_2CH_2$—.

In still another embodiment of the third aspect of the invention, the compounds of the present invention are described by formula (I) or a pharmaceutically acceptable salt thereof, wherein Ar is a phenyl ring, optionally substituted by one or two substituents, each substituent independently is halogen, $C_{1-4}$alkyl, or oxy$C_{1-4}$alkyl;

$R_1$ is —$CH_2$— connected via $B_2$ to $R_3$;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_3$ is —$CH_2$— connected via $B_2$ to $R_1$;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is absent; and $B_2$ is —CH=CH—.

In another embodiment of the third aspect of the invention, the compounds of the present invention are described by formula (I) or a pharmaceutically acceptable salt thereof, wherein Ar is a phenyl ring, optionally substituted by one or two substituents, each substituent independently is halogen, $C_{1-4}$alkyl, or oxy$C_{1-4}$alkyl;

$R_1$ is —$CH_2$— connected via $B_2$ to $R_3$;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_3$ is —CH= connected via $B_2$ to $R_1$;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is absent; and $B_2$ is =CH—.

In a fourth aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is —NH—, —$NR_4$—, or —$NR_5$— connected via $B_1$ to $R_2$;

$R_2$ is —$CH_2$— or —CH= connected via $B_1$ to $R_1$;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is —$CH_2$—, =CH—, —$CH_2CH_2$—, or —CH=CH— and $B_2$ is absent.

In an embodiment of the fourth aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is —NH—, —$NR_4$—, or —$NR_5$— connected via $B_1$ to $R_2$;

$R_2$ is —$CH_2$— connected via $B_1$ to $R_1$;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is —$CH_2$—, and $B_2$ is absent.

In yet another embodiment of the fourth aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is —NH—, —$NR_4$—, or —$NR_5$— connected via $B_1$ to $R_2$;

$R_2$ is —$CH_2$— connected via $B_1$ to $R_1$;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is —$CH_2CH_2$—; and $B_2$ is absent.

In still another embodiment of the fourth aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is —NH—, —$NR_4$—, or —$NR_5$— connected via $B_1$ to $R_2$;

$R_2$ is —$CH_2$— connected via $B_1$ to $R_1$;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is —CH=CH— and $B_2$ is absent.

In an embodiment of the fourth aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is —NH—, —$NR_4$—, or —$NR_5$— connected via $B_1$ to $R_2$;

$R_2$ is —CH= connected via $B_1$ to $R_1$;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is =CH—; and $B_2$ is absent.

In a fifth aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is —NH—, —NR$_4$—, or —NR$_5$— connected via $B_2$ to $R_3$;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_3$ is —CH$_2$— or —CH= connected via $B_2$ to $R_1$;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is absent; and $B_2$ is —CH$_2$—, =CH—, —CH$_2$CH$_2$—, or —CH=CH—.

In an embodiment of the fifth aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is —NH—, —NR$_4$—, or —NR$_5$— connected via $B_2$ to $R_3$;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_3$ is —CH$_2$— connected via $B_2$ to $R_1$;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is absent; and $B_2$ is —CH$_2$—.

In yet another embodiment of the fifth aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is —NH—, —NR$_4$—, or —NR$_5$— connected via $B_2$ to $R_3$;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_3$ is —CH= connected via $B_2$ to $R_1$;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is absent; and $B_2$ is =CH—.

In still another embodiment of the fifth aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is —NH—, —NR$_4$—, or —NR$_5$— connected via $B_2$ to $R_3$;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_3$ is —CH$_2$— connected via $B_2$ to $R_1$;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is absent; and $B_2$ is —CH$_2$CH$_2$—.

In another embodiment of the fifth aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is —NH—, —NR$_4$—, or —NR$_5$— connected via $B_2$ to $R_3$;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_3$ is —CH$_2$— connected via $B_2$ to $R_1$;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is absent; and $B_2$ is —CH=CH—.

In a sixth aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is =N— connected via $B_1$ to $R_2$;

$R_2$ is —CH$_2$— or —CH= connected via $B_1$ to $R_1$;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is —CH$_2$—, =CH—, —CH$_2$CH$_2$—, or —CH=CH— and $B_2$ is absent.

In an embodiment of the sixth aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is =N— connected via $B_1$ to $R_2$;

$R_2$ is —CH$_2$— connected via $B_1$ to $R_1$;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is —CH$_2$— and $B_2$ is absent.

In yet another embodiment of the sixth aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is =N— connected via $B_1$ to $R_2$;

$R_2$ is —CH$_2$— connected via $B_1$ to $R_1$;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is —CH$_2$CH$_2$— and $B_2$ is absent.

In still another embodiment of the sixth aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is =N— connected via $B_1$ to $R_2$;

$R_2$ is —CH= connected via $B_1$ to $R_1$;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is =CH—, and $B_2$ is absent.

In another embodiment of the sixth aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is =N— connected via $B_1$ to $R_2$;

$R_2$ is —CH$_2$— connected via $B_1$ to $R_1$;

$R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is —CH=CH— and $B_2$ is absent.

In a seventh aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is =N— connected via $B_2$ to $R_3$;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_3$ is —CH$_2$— or —CH= connected via $B_2$ to $R_1$;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is absent; and $B_2$ is —CH$_2$—, =CH—, —CH$_2$CH$_2$—, or —CH=CH—.

In an embodiment of the seventh aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is =N— connected via $B_2$ to $R_3$;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_3$ is —CH$_2$— connected via $B_2$ to $R_1$;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is absent; and $B_2$ is —CH$_2$—.

In still another embodiment of the seventh aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is =N— connected via $B_2$ to $R_3$;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_3$ is —CH= connected via $B_2$ to $R_1$;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is absent; and $B_2$ is =CH—.

In yet another embodiment of the seventh aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is =N— connected via $B_2$ to $R_3$;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_3$ is —CH$_2$— connected via $B_2$ to $R_1$;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_6$ is a phenyl group, a $C_{1-4}$alkylphenyl group, or absent;

$R_7$ is a phenyl group, a $C_{1-4}$alkylphenyl group, or absent;

$B_1$ is absent; and $B_2$ is —CH$_2$CH$_2$—.

In still another embodiment of the seventh aspect of the invention, the compounds of the invention are represented by formula (I), or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl;

$R_1$ is =N— connected via $B_2$ to $R_3$;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_3$ is —CH$_2$— connected via $B_2$ to $R_1$;

$R_4$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

$R_5$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl;

R₆ is a phenyl group, a $C_{1-4}$alkylphenyl group, or absent;
R₇ is a phenyl group, a $C_{1-4}$alkylphenyl group, or absent;
B₁ is absent; and
B₂ is —CH=CH—.

The term "halogen" includes fluorine, chlorine, bromine and iodine atoms.

The term "aryl group" includes single and fused multiple aromatic rings. Heteroatoms can optionally be included in the rings. Examples of aryl groups are phenyl, naphthyl, pyridinyl, pyridazinyl, pyrimidinyl, pyrazinyl, imidazolyl, quinoxalinyl, furyl, thienyl, pyrrolyl, benzimidazolyl, indolyl, quinolinyl, isoquinolinyl, pyrazolyl, indazolyl, oxazolyl, isoxazolyl, thiazolyl, isothiazolyl, oxadiazolyl, thiadiazolyl, triazolyl, tetrazolyl, imidazolyl, benzthienyl, and benzofuryl.

The term "optionally substituted" is intended to include both substituted and unsubstituted. Thus, for example, optionally substituted aryl could represent a pentafluorophenyl or a phenyl ring. Further, optionally substituted multiple moieties such as, for example, alkylaryl are intended to mean that the aryl and the aryl groups are optionally substituted. If only one of the multiple moieties is optionally substituted then it will be specifically recited such as "an alkylaryl, the aryl optionally substituted with halogen or hydroxyl."

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.01 mg/kg to about 140 mg/kg of body weight per day are useful in the treatment of pain, migraine, depression, anxiety, schizophrenia, Parkinson's disease, stroke, and in the treatment of neurophathic conditions such as postherpetic neuralgia, central pain from spinal cord injury, and phantom limb pain which are responsive to NOVA NR2B inhibition, or alternatively about 0.5 mg to about 7 g per patient per day. For example, inflammation may be effectively treated by the administration of from about 0.01 mg to 50 mg of the compound per kilogram of body weight per day, or alternatively about 0.5 mg to about 3.5 g per patient per day. Further, it is understood that the NR2B antagonist compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 500 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions of this invention have been found to exhibit biological activity as NR2B antagonists. Accordingly, another aspect of the invention is the treatment in mammals of, for example, pain, migraine, depression, anxiety, schizophrenia, Parkinson's disease, stroke, and neuropathic conditions such as posterpetic neuralgia, central pain from spinal cord injury, and phantom limb pain—maladies that are amenable to amelioration through NMDA NR2B inhibition—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

EXAMPLES

The following Examples 1–29 are shown as trifluoroacetic acid ("TFA") salts. The trifluoroacetic acid salt form arose from the HPLC procedure and not because the salt per se was desired. The free bases of the trifluoroacetic acid salts can be readily obtained by the following procedure. Dissolve the salt in a 1:1 mixture of ethyl acetate and saturated aqueous sodium bicarbonate, separate the layers, dry the organic part over $Na_2SO_4$ and concentrate. The resulting residue is the base of the starting trifluoroacetic acid salt.

Example 1

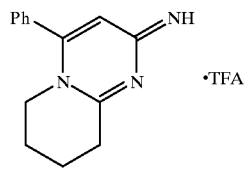

Example 1 was prepared by the following method, Procedure A: A solution of 2-iminopiperidine (60 mg, 0.61 mmol) was dissolved in 5% MeCN/THF (5 mL) at room temperature. 3-Phenyl-2-propynenitrile (77 mg, 0.61 mmol) was added in one portion and the resulting reaction mixture was stirred 2 h. The reaction mixture was poured into ethyl acetate and aqueous $NaHCO_3$. The layers were separated. The organic layer was dried over $Na_2SO_4$, filtered and concentrated. The residue was purified by preparative reverse phase HPLC to give Example 1 (134 mg, 65% yield as a white solid: $^1H$ NMR (500 MHz, $CDCl_3$) δ 9.42 (br s, 1H), 7.58-7.50 (m, 3H), 7.38-7.35 (m 2H), 6.81 (s 1H), 6.73 (br s, 1H), 3.84 (t, J=5.8 Hz, 2H), 3.10 (t, J=6.6 Hz, 2H), 2.03-1.94 (m, 4H) ppm; $^{13}C$ NMR (125 MHz, $CDCl_3$) δ 163.5, 163.0, 157.4, 131.5, 130.6, 129.5, 128.3, 106.6, 50.3, 31.5, 21.8, 18.1, ppm; high resolution mass spectrum m/z 226.1353 [(M+H)$^+$; calc'd for $C_{14}H_{16}N_3$: 226.1339].

Example 2

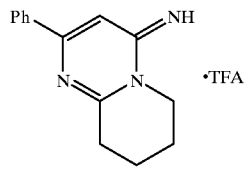

Example 2 was prepared by the following method, Procedure B: A solution of 2-iminopiperidine (60 mg, 0.61 mmol) was dissolved in 5% MeCN/THF (5 mL) at room temperature. NaHMDS (1.0M/THF, 1.22 mL. 1.22 mmol) was added dropwise and the resulting solution was stirred at room temperature for 5 min. 3-Phenyl-2-propynenitrile (77 mg, 0.61 mmol) was then added in one portion, the reaction mixture turned dark red and was stirred for 5 min. The reaction mixture was poured onto ethyl acetate and aqueous $NaHCO_3$ and the layers separated. The organic layer was dried over $Na_2SO_4$, filtered and concentrated. The residue was purified by preparative reverse HPLC to give Example 2 (107 mg, 52% yield) as a white solid: $^1H$ NMR (500 MHz, $CDCl_3$) δ 9.74 (br s, 1H), 9.18 (br s, 1H), 8.04 (dd, J=7.8, 1.5 Hz, 2H), 7.56-7.43 (m, 4H), 4.10 (t, J=6.2 Hz, 2H), 3.13 (t, J=6.5 Hz, 2H), 2.18-2.11 (m, 2H), 2.02-1.98 (m, 2H) ppm; $^{13}C$ NMR (125 MHz), $CDCl_3$) δ 161.2, 158.3, 157.7, 132.2, 129.1, 129.0, 127.5, 101.4, 47.0, 32.3, 21.4, 18.1, ppm; high resolution mass spectrum m/z 226.1351 [(M+H)$^+$; calc'd for $C_{14}H_{16}N_3$: 226.1339].

Example 3

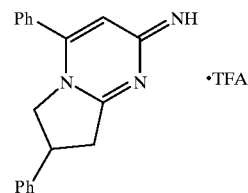

Example 3 was prepared by following procedure A except using 4-phenyl-pyrrolidin-2-ylidene instead of 2-iminopiperidine. (61% yield): $^1H$ NMR (500 MHz, $CDCl_3$) δ 10.39 (br s, 1H), 9.63 (br s, 1H), 7.51-7.46 (m, 5H), 7.36-7.28 (m, 3H); 7.24 (, 2H), 7.04 (s, 1H); 4.48 (dd, 1H), 4.25 (dd, 1H), 3.90 (quint, 1H), 3.58 (dd, 1H), 3.48 (dd, 1H) ppm; $^{13}C$ NMR (125 MHz), $CDCl_3$) δ 166.8, 165.5, 154.2, 138.1, 131.8, 130.2, 129.5, 129.4, 128.3, 128.2, 127.0, 104.9, 59.0, 39.7, 39.5 ppm; mass spectrum m/z 288 [(M+H)$^+$; calc'd for $C_{19}H_{18}N_3$: 288].

Example 4

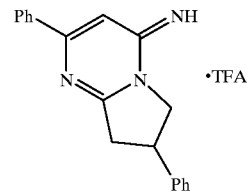

Example 4 was prepared by following procedure B except using 4-phenyl-pyrrolidin-2-ylidene instead of 2-iminopiperidine. (63% yield): $^1H$ NMR (500 MHz, $CDCl_3$) δ 10.02 (br s, 1H), 9.67 (br s, 1H), 8.07 (d, 2H), 7.61-7.49 (m, 4H), 7.38-7.32 (m, 3H), 7.24 (m, 2H), 4.97 (dd, 1H), 4.35 (dd, 1H), 4.01 (quint, 1H), 3.66 (dd, 1H), 3.41 (dd, 1H) ppm; $^{13}C$ NMR (125 MHz), $CDCl_3$) δ 163.3, 162.4, 155.8, 138.6, 134.4, 132.3, 129.4, 129.2, 128.2, 127.8, 126.8, 101.8, 55.8, 39.3, 38.5 ppm; mass spectrum m/z 288 [(M+H)$^+$; calc'd for $C_{19}H_{18}N_3$: 288].

Example 5

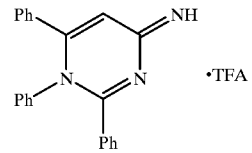

Example 5 was prepared by following procedure A except using N-phenyl-benzamidine instead of 2-iminopiperidine.

(25% yield): mass spectrum m/z 324 [(M+H)⁺; calc'd for C₂₂H₁₈N₃: 324].

Example 6

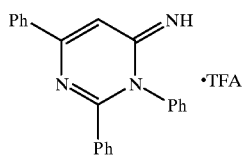

Example 6 was prepared by following procedure B except N-phenyl-benzamidine instead of 2-iminopiperidine. (31% yield): mass spectrum m/z 324 [(M+H)⁺; calc'd for C₂₂H₁₈N₃: 324].

Example 7

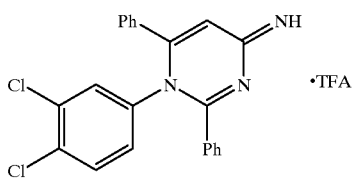

Example 7 was prepared by following procedure A except using N-(3,4-dichloro-phenyl)-benzamidine instead of 2-iminopiperidine. (5% yield): mass spectrum m/z 393 [(M+H)⁺; calc'd for C₂₂H₁₆Cl₂N₃: 393].

Example 8

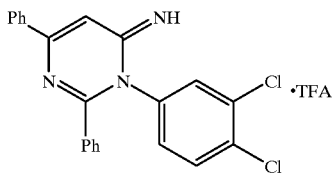

Example 8 was prepared by following procedure B except using N-(3,4-dichloro-phenyl)-benzamidine instead of 2-iminopiperidine. (32% yield): mass spectrum m/z 393 [(M+H)⁺; calc'd for C₂₂H₁₆Cl₂N₃: 393].

Example 9

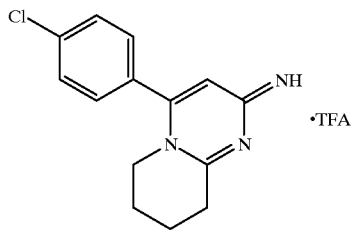

Example 9 was prepared by following procedure A except using 3-(4-chloro-phenyl)-2-propynenitrile instead of 3-phenyl-2-propynenitrile. (52% yield): ¹H NMR (300 MHz, CD₃OD) δ 7.61 (d, 2H), 7.53 (d, 2H), 6.57 (s 1H), 3.81 (t, 2H), 3.10 (t, 2H), 1.95 (m, 4H) ppm; mass spectrum m/z 260 [(M+H)⁺; calc'd for C₁₄H₁₅ClN₃: 260].

Example 10

L-452493-001X

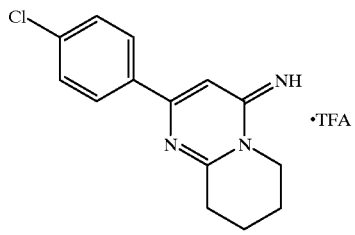

Example 10 was prepared by following procedure B except using 3-(4-chloro-phenyl)-2-propynenitrile instead of 3-phenyl-2-propynenitrile. (61% yield): ¹H NMR (300 MHz, CD₃OD) δ 8.13 (d, 2H), 7.55 (d, 2H), 7.30 (s, 1H), 3.99 (t, 2H), 3.20 (t, 2H), 2.18 (m, 2H), 2.01 (m, 2H) ppm; mass spectrum m/z 260 [(M+H)⁺; calc'd for C₁₄H₁₅ClN₃: 260].

Example 11

L-453449-001G

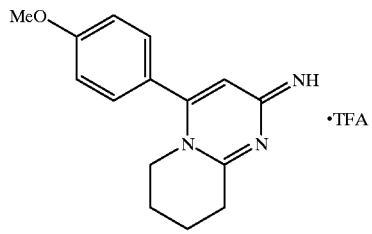

Example 11 was prepared by following procedure A except using 3-(4-methoxy-phenyl)-2-propynenitrile instead of 3-phenyl-2-propynenitrile. (60% yield): ¹H NMR (300 MHz, CD₃OD) δ 7.44 (d, 2H), 7.12 (d, 2H), 6.57 (s 1H), 3.90 (t, 2H), 3.86 (s, 3H), 3.10 (t, 2H), 1.97 (m, 4H) ppm; mass spectrum m/z 256 [(M+H)⁺; calc'd for C₁₅H₁₈N₃O: 256].

Example 12

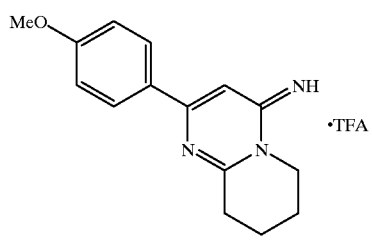

Example 12 was prepared by following procedure B except using 3-(4-methoxy-phenyl)-2-propynenitrile instead of 3-phenyl-2-propynenitrile. (55% yield): ¹H NMR (300 MHz, CD₃OD) δ 8.10 (d, 2H), 7.19 (s, 1H), 7.05 (d, 2H), 3.97 (t, 2H), 3.89 (s, 3H), 3.17 (t, 2H), 2.18 (m, 2H), 2.00 (m, 2H) ppm; mass spectrum m/z 256 [(M+H)⁺; calc'd for C₁₅H₁₈N₃O: 256].

Example 13

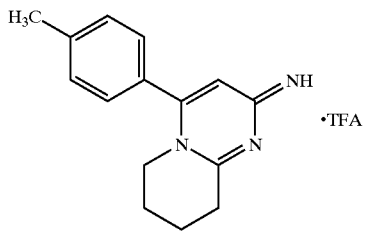

Example 13 was prepared by following procedure A except using 3-(4-methyl-phenyl)-2-propynenitrile instead of 3-phenyl-2-propynenitrile. (56% yield): $^1$H NMR (300 MHz, CD$_3$OD) δ 7.40 (m, 4H), 6.57 (s 1H), 3.85 (t, 2H), 3.10 (t, 2H), 2.41 (s, 3H), 1.96 (m, 4H) ppm; mass spectrum m/z 240 [(M+H)$^+$; calc'd for C$_{15}$H$_{18}$N$_3$: 240].

Example 14

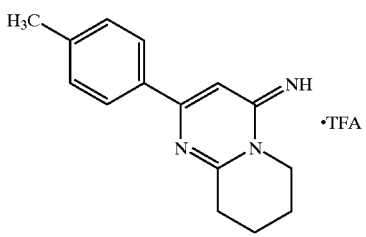

Example 14 was prepared by following procedure B except using 3-(4-methyl-phenyl)-2-propynenitrile instead of 3-phenyl-2-propynenitrile. (58% yield): $^1$H NMR (300 MHz, CD$_3$OD) δ 8.01 (d, 2H), 7.35 (d, 2H), 7.22 (s, 1H), 3.98 (t, 2H), 3.18 (t, 2H), 2.18 (m, 2H), 2.00 (m, 2H) ppm; mass spectrum m/z 240 [(M+H)$^+$; calc'd for C$_{15}$H$_{18}$N$_3$: 240].

Example 15

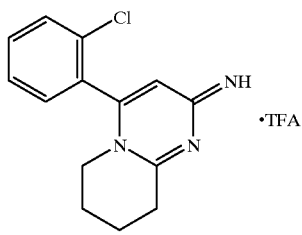

Example 15 was prepared by following procedure A except using 3-(2-chloro-phenyl)-2-propynenitrile instead of 3-phenyl-2-propynenitrile. (15% yield): $^1$H NMR (300 MHz, CD$_3$OD) δ 7.78-7.44 (m, 4H), 6.58 (s 1H), 3.77 (m, 2H), 3.12 (m, 2H), 1.98 (m, 4H) ppm; mass spectrum m/z 260 [(M+H)$^+$; calc'd for C$_{14}$H$_{15}$ClN$_3$: 260].

Example 16

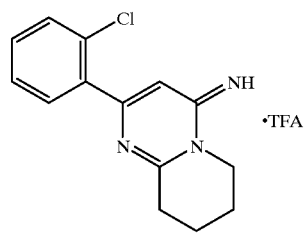

Example 16 was prepared by following procedure B except using 3-(2-chloro-phenyl)-2-propynenitrile instead of 3-phenyl-2-propynenitrile. (48% yield): $^1$H NMR (300 MHz, CD$_3$OD) δ 7.77 (d, 1H), 7.60-7.43 (m, 3H), 7.28 (s, 1H), 4.02 (t, 2H), 3.18 (t, 2H), 2.20 (m, 2H), 2.03 (m, 2H) ppm; mass spectrum m/z 260 [(M+H)$^+$; calc'd for C$_{14}$H$_{15}$ClN$_3$: 260].

Example 17

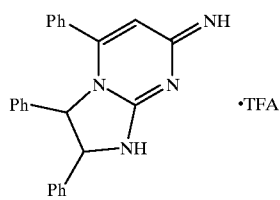

Example 17 was prepared by the following procedure. A solution of 4,5-diphenyl-imidazolidin-2-ylideneamine hydrobromide (50 mg, 0.16 mmol) was dissolved in ethyl acteate and washed with aqueous NaHCO3. The organic layer was dried over MgSO4, filtered and concentrated. The residue was then dissolved in EtOH (1 mL) at room temperature. 3-Phenyl-2-propynenitrile (25 mg, 0.19 mmol) was added in one portion and the resulting reaction mixture was heated to 90 C. and stirred for 15 h. The reaction mixture was concentrated and the residue was purified by preparative reverse phase HPLC to give Example 17: $^1$H NMR (300 MHz, CDCl$_3$) δ 9.50 (s, 1H), 9.35 (s, 1H), 9.07 (s, 1H), 7.40-6.90 (m, 13H), 6.37 (d, 2H), 6.21 (s, 1H), 5.77 (d, 2H), 5.56 (d, 2H) ppm; mass spectrum m/z 365 [(M+H)$^+$; calc'd for C$_{24}$H$_{21}$N$_4$: 365].

Example 18

L-425037-001E

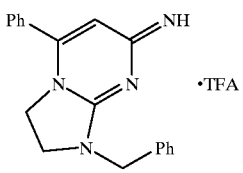

Example 18 was prepared by the following procedure. A solution of 1-benzyl-imidazolidin-2-ylideneamine (35 mg, 0.2 mmol) was dissolved in MeCN (2 mL) at room temperature. 3-Phenyl-2-propynenitrile (25 mg, 0.2 mmol) was added in one portion and the resulting reaction mixture was stirred for 1 h. The reaction mixture was poured into ethyl acetate and aqueous K$_2$CO$_3$. The layers were separated. The organic layer was dried over Na$_2$SO$_4$, filtered and concentrated. The residue was purified by preparative reverse phase HPLC. Two products were isolated (Example 17 and Example 18). Example 18 is the major product: $^1$H NMR (300 MHz, CDCl$_3$) δ 7.60-7.28 (m, 10H), 6.40 (s, 1H), 4.66 (s, 2H), 4.11 (t, 2H), 3.69 (t, 2H) ppm; mass spectrum m/z 303 [(M+H)$^+$; calc'd for C$_{19}$H$_{19}$N$_4$: 303].

Example 19

L-425038-001N

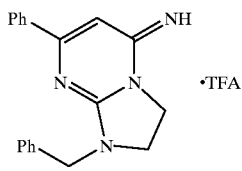

Example 19 was prepared by following the procedure given in Example 18. Example 19 was the minor product is the above reaction: $^1$H NMR (300 MHz, CDCl$_3$) δ 8.05 (d, 2H), 7.58-7.30 (m, 8H), 6.62 (s, 1H), 4.78 (s, 2H), 4.24 (m, 2H), 3.82 (m, 2H) ppm; mass spectrum m/z 303 [(M+H)$^+$; calc'd for C$_{19}$H$_{19}$N$_4$: 303].

Example 20

L-425649-001Y

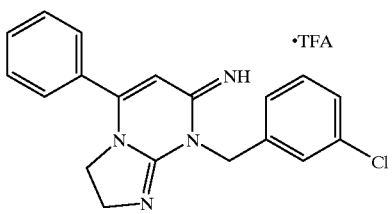

Example 20 was prepared by the following procedure. A solution of (3-chloro-benzyl)-(4,5-dihydro-1H-imidazol-2-yl)-amine (25 mg, 0.12 mmol) was dissolved in MeCN (2 mL) at room temperature. 3-Phenyl-2-propynenitrile (15 mg, 0.12 mmol) was added in one portion and the resulting reaction mixture was stirred for 15 h. The reaction mixture was concentrated and purified by preparative reverse phase HPLC to give example 20: $^1$H NMR (300 MHz, CDCl$_3$) δ 7.65-7.27 (m, 8H), 5.89 (s, 1H), 5.27 (s, 2H), 4.20-4.00 (m, 4H) ppm; mass spectrum m/z 337 [(M+H)$^+$; calc'd for C$_{19}$H$_{18}$ClN$_4$: 337].

Example 21

L-425652-001E

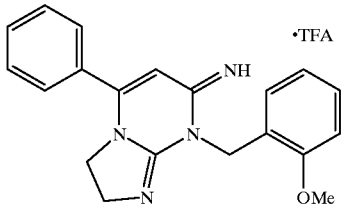

Example 21 was prepared by following the procedure for Example 20 except using (2-methoxy-benzyl)-(4,5-dihydro-1H-imidazol-2-yl)-amine instead of (3-chloro-benzyl)-(4,5-dihydro-1H-imidazol-2-yl)-amine: mass spectrum m/z 333 [(M+H)$^+$; calc'd for C$_{20}$H$_{21}$N$_4$O: 333].

Example 22

L-425653-001N

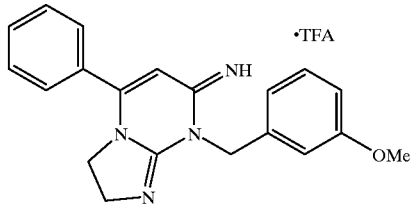

Example 22 was prepared by following the procedure for Example 20 except using (3-methoxy-benzyl)-(4,5-dihydro-1H-imidazol-2-yl)-amine instead of (3-chloro-benzyl)-(4,5-dihydro-1H-imidazol-2-yl)-amine: mass spectrum m/z 333 [(M+H)$^+$; calc'd for C$_{20}$H$_{21}$N$_4$O: 333].

Example 23

L-425654-001X

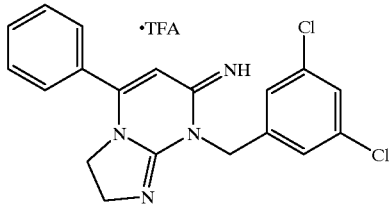

Example 23 was prepared by following the procedure for Example 20 except using (3,5-dichloro-benzyl)-(4,5- dihydro-1H-imidazol-2-yl)-amine instead of (3-chloro-benzyl)-(4,5-dihydro-1H-imidazol-2-yl)-amine: mass spectrum m/z 371 [(M+H)$^+$; calc'd for C$_{19}$H$_{17Cl2}$N$_4$: 371].

Example 24

L-425656-001P

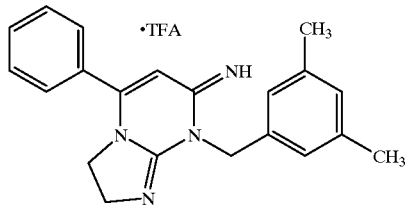

Example 24 was prepared by following the procedure for Example 20 except using (3,5-dimethyl-benzyl)-(4,5-dihydro-1H-imidazol-2-yl)-amine instead of (3-chloro-benzyl)-(4,5-dihydro-1H-imidazol-2-yl)-amine: mass spectrum m/z 331 [(M+H)$^+$; calc'd for C$_{21}$H$_{23}$N$_4$: 331].

Example 25

L426021-001E

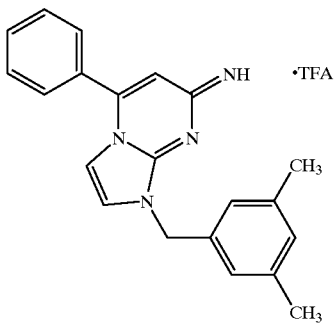

Example 25 was prepared by the following procedure. A solution of 5-phenyl-8H-imidazo[1,2-a]pyrimidin-7-ylideneamine (10 mg, 0.05 mmol) was dissolved in xylene (2 mL) at room temperature. 3,5-Dimethyl benzyl bromide (10 mg, 0.05 mmol) was added in one portion and the resulting reaction mixture was heated to 140 C. and stirred for 1 h. The reaction mixture was concentrated and purified by preparative reverse phase HPLC to give example 25: $^1$H NMR (300 MHz, CDCl$_3$) δ 9.39 (br s, 1H), 7.60 (s, 5H), 7.24 (s, 1H), 7.19 (s, 1H), 7.08 (m, 2H), 6.95 (s, 2H), 6.25 (br s, 1H), 5.21 (s, 2H), 2.35 (s, 6H) ppm; mass spectrum m/z 329 [(M+H)$^+$; calc'd for C$_{21}$H$_{21}$N$_4$: 329].

Example 26

L-426022-001N

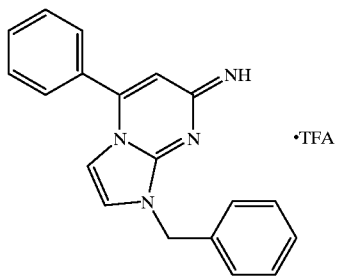

Example 26 was prepared by following the procedure for Example 25 except using benzyl bromide instead of 3,5-dimethyl benzyl bromide: mass spectrum m/z 301 [(M+H)$^+$; calc'd for C$_{19}$H$_{17}$N$_4$: 301].

Example 27

L-426023-001X

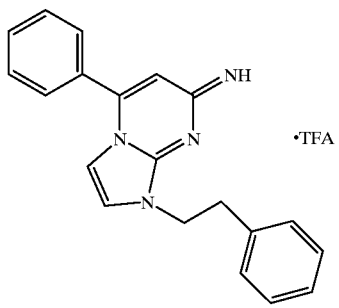

Example 27 was prepared by following the procedure for Example 25 except using phenethyl bromide instead of 3,5-dimethyl benzyl bromide: mass spectrum m/z 315 [(M+H)$^+$; calc'd for C$_{20}$H$_{19}$N$_4$: 315].

Example 28

L-426666-001B

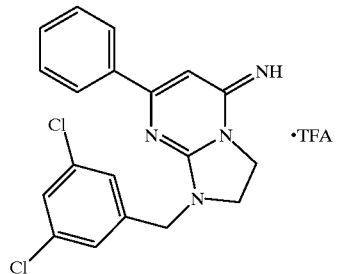

Example 28 was prepared by the following procedure. A solution of 1-(3,5-dichloro-benzyl)-imidazolidin-2-ylideneamine (30 mg, 0.12 mmol) was dissolved in MeCN (3 mL) at room temperature. 3-Phenyl-2-propynenitrile (15 mg, 0.12 mmol) was added in one portion and the resulting reaction mixture was stirred for 1 h. The reaction mixture was concentrated and purified by preparative reverse phase HPLC to give Example 28: $^1$H NMR (300 MHz, CDCl$_3$) δ 8.65 (br s, 1H), 8.00 (d, 2H), 7.55-7.42 (m, 3H), 7.25 (m, 3H), 6.78 (s, 1H), 6.30 (br s, 1H), 4.66 (s, 2H), 4.45 (t, 2H), 3.80 (t, 2H) ppm; mass spectrum m/z 372 [(M+H)$^+$; calc'd for C$_{19}$H$_{17Cl2}$N$_4$: 372].

Example 29

L-429067-001K

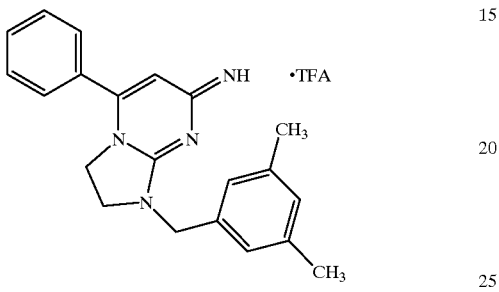

Example 29 was prepared by the following procedure. A solution of 5-phenyl-2,3-dihydro-1H-imidazo[1,2-a]pyrimidin-7-ylideneamine (12 mg, 0.05 mmol) was dissolved in xylene (2 mL) at room temperature. 3,5-Dimethyl benzyl bromide (10 mg, 0.05 mmol) was added in one portion and the resulting reaction mixture was heated to 140 C. and stirred for 1 h. The reaction mixture was concentrated and purified by preparative reverse phase HPLC to give example 29: $^1$H NMR (300 MHz, CDCl$_3$) δ 7.59 (s, 5H), 7.00 (s, 3H), 6.05 (s, 1H), 4.65 (s, 2H), 4.18 (dd, 2H), 3.70 (dd, 2H), 2.32 (s, 6H) ppm; mass spectrum m/z 331 [(M+H)$^+$; calc'd for C$_{21}$H$_{23}$N$_4$: 331].

Examples 30–58 are prepared by forming the free base compound from the above Examples 1–29:

Example 30

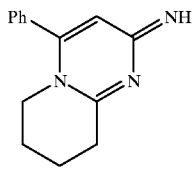

Example 31

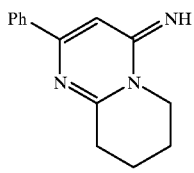

Example 32

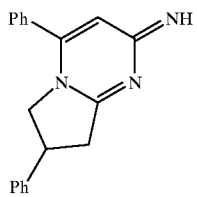

Example 33

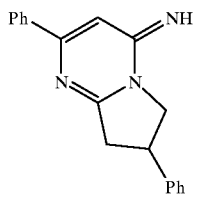

Example 34

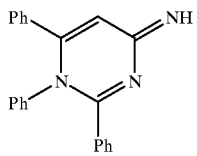

Example 35

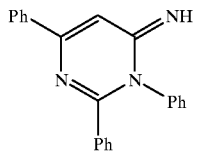

Example 36

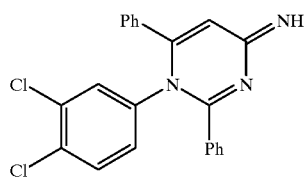

Example 37

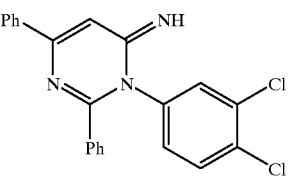

Example 38
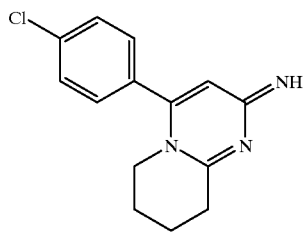
Example 39
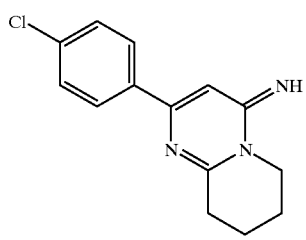
Example 40
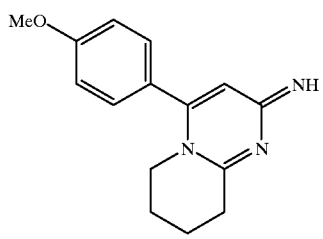
Example 41
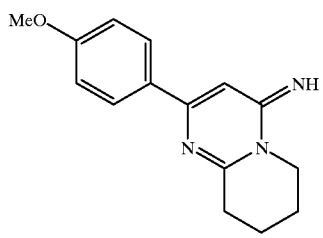
Example 42
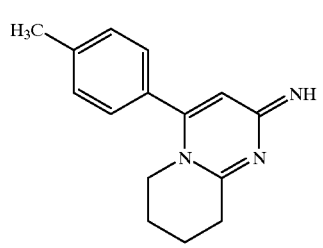
Example 43
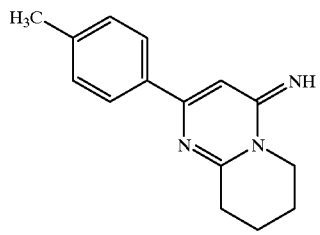
Example 44
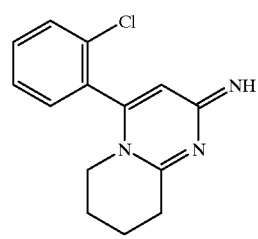
Example 45
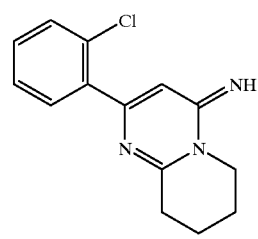
Example 46
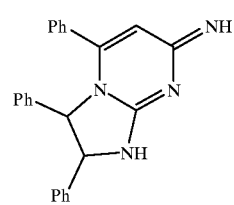
Example 47
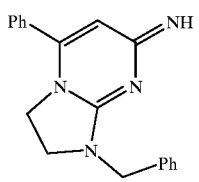

Example 48
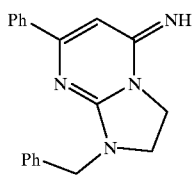
Example 49
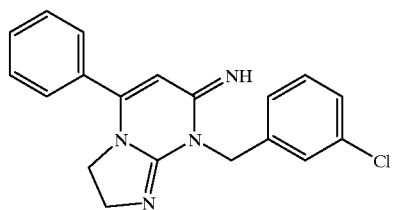
Example 50
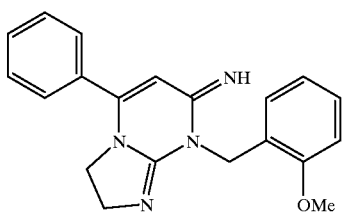
Example 51
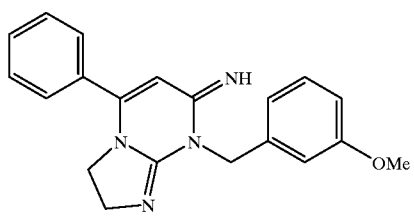
Example 52
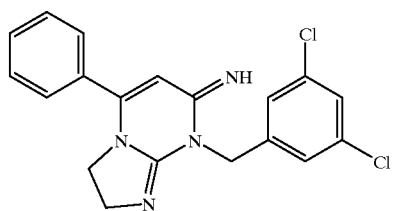
Example 53
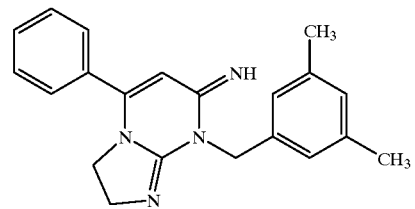
Example 54
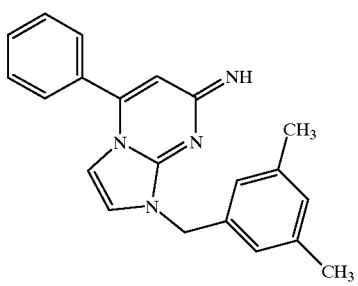
Example 55
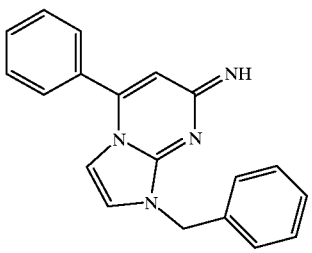
Example 56
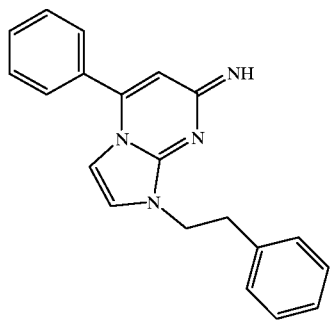

Example 57

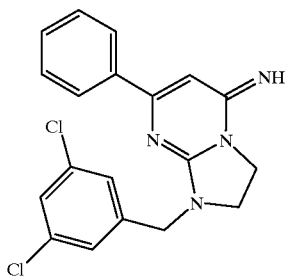

Example 58

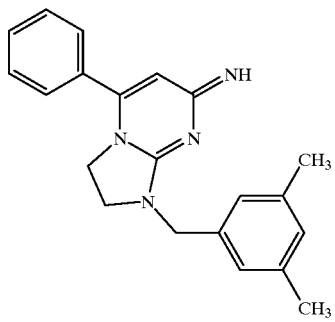

What is claimed is:

1. A compound represented by formula (I):

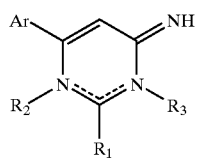
(I)

or a pharmaceutically acceptable salt thereof, wherein

Ar is an aromatic group, said aromatic group being phenyl, naphthyl, pyridinyl, pyridazinyl, pyrimidinyl, pyrazinyl, imidazolyl, quinoxalinyl, furyl, thienyl, pyrrolyl, benzimidazolyl, indolyl, quinolinyl, isoquinolinyl, pyrazolyl, indazolyl, oxazolyl, isoxazolyl, thiazolyl, isothiazolyl, oxadiazolyl, thiadiazolyl, triazolyl, tetrazolyl, imidazolyl, benzthienyl, or benzofuryl, said aromatic group optionally substituted by one or two substituents, each substituent independently is halogen, $C_{1-4}$alkyl, or oxy$C_{1-4}$alkyl;

$R_1$ is a phenyl;

$R_2$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl; and $R_3$ is a phenyl group, a $C_{1-4}$alkylphenyl group, or absent, wherein the groups optionally may be substituted by one or two substituents, each substituent is independently halogen, $C_{1-4}$alkyl, or oxy$C_{1-4}$alkyl.

2. The compound according to claim 1, or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl.

3. The compound according to claim 1, or a pharmaceutically acceptable salt thereof, wherein:

Ar is a phenyl ring, optionally substituted by one or two substituents, each substituent independently is halogen, $C_{1-4}$alkyl, or oxy$C_{1-4}$alkyl.

4. The compound according to claim 3, or a pharmaceutically acceptable salt thereof, wherein:

$R_3$ is absent.

5. The compound according to claim 3, or a pharmaceutically acceptable salt thereof, wherein $R_2$ is absent.

6. A compound represented by:

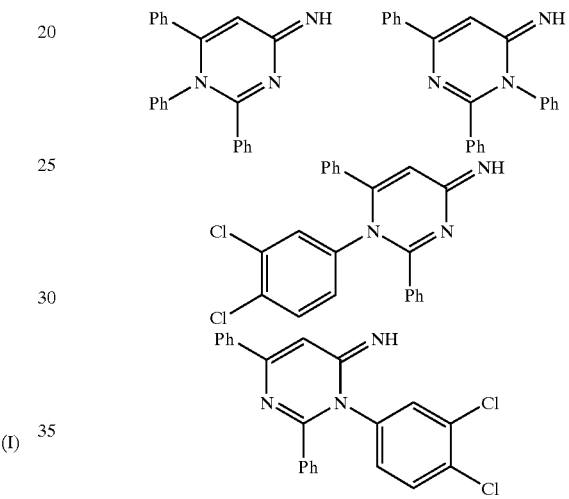

or a pharmaceutically acceptable salt thereof.

7. A compound represented by

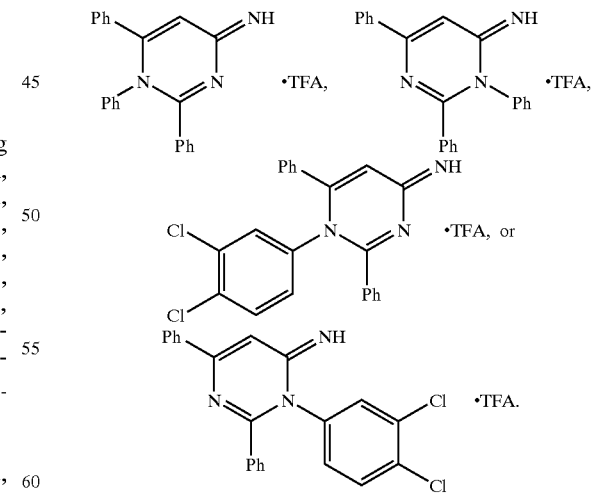

8. A method of treatment of Parkinson's disease comprising the step of administering a therapeutically effective amount of a compund according to claim 1, or a pharmaceutically acceptable salt thereof.

* * * * *